United States Patent [19]

Andrews et al.

[11] 4,113,854

[45] Sep. 12, 1978

[54] PROPHYLACTIC TREATMENT OF MASTITIS

[75] Inventors: Jeffrey F. Andrews, Egan; Therese A. Mullin, Minneapolis; Raymond Senkus, Stillwater, all of Minn.

[73] Assignee: Minnesota Mining and Manufacturing Company, Saint Paul, Minn.

[21] Appl. No.: 758,342

[22] Filed: Jan. 10, 1977

[51] Int. Cl.$^2$ .................. A61K 31/78; A61K 31/74; C08L 5/00

[52] U.S. Cl. .................. 424/81; 260/17.4 R; 424/78; 424/83

[58] Field of Search ............... 424/78, 81; 260/17.4 R

[56] References Cited

U.S. PATENT DOCUMENTS

| | | | |
|---|---|---|---|
| 3,100,180 | 8/1963 | Smith et al. ........................... | 424/78 |
| 3,627,871 | 12/1971 | Groves et al. ........................ | 424/78 |
| 3,740,360 | 6/1973 | Nimerick ......................... | 260/17.4 R |
| 3,743,613 | 7/1973 | Coulter et al. .................. | 260/17.4 R |

FOREIGN PATENT DOCUMENTS 6,805,856  2/1968  Netherlands.

*Primary Examiner*—Sam Rosen
*Attorney, Agent, or Firm*—Cruzan Alexander; Donald M. Sell; Carolyn A. Bates

[57] ABSTRACT

A method is disclosed for the prophylactic treatment of mastitis in milk-producing animals. The method comprises dipping the teats of the animal into a composition comprising a film-forming polymer latex and a water-soluble polymer thickening agent in an aqueous medium. The composition has a thixotropic value of 15 to 1200 dynes/cm$^2$ and an upper viscosity limit of 10 poise at a shear rate of 250 sec$^{-1}$.

14 Claims, 1 Drawing Figure

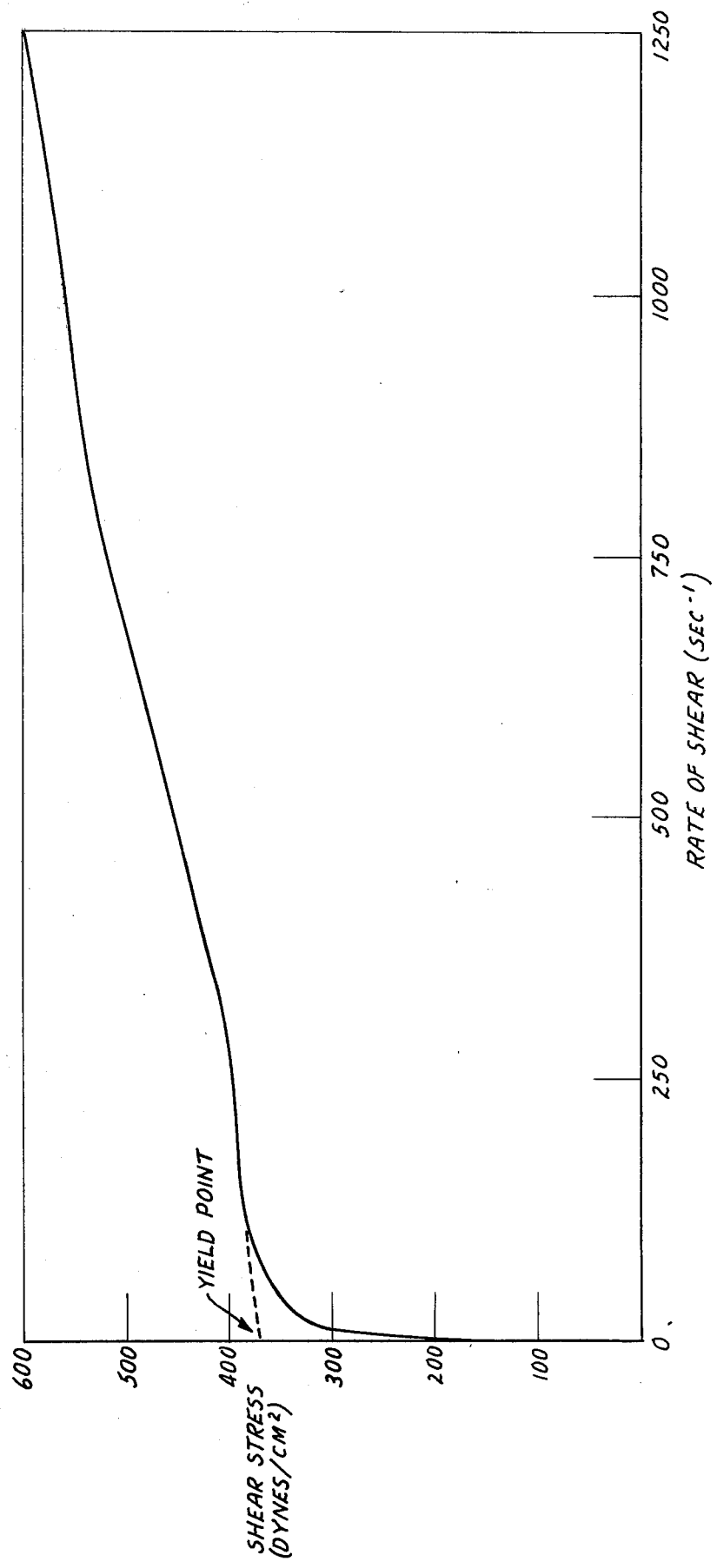

PROPHYLACTIC TREATMENT OF MASTITIS

This invention relates to a method of preventing mastitis in milk producing animals. More particularly it relates to a method of coating the teats of such animals to provide a physical barrier against mastitis-causing agents. Compositions for carrying out this method are also included within the scope of the invention.

Two primary requirements of good dairy herd management are maintaining the animal's teats in good physical condition and keeping the teats free from infection. The teats are often irritated by abrasion, windburn and sunburn. This irritation, harmful in itself, also facilitates infection of the teat by pathogenic organisms, thereby leading to decreased milk productivity, loss of milk and even destruction of the animal. Infection of the teat is commonly called "mastitis," a generic term used to signify an inflammation of the animal's mammary gland without specifying the nature of the infection or the type of organism causing the inflammation. Once mastitis occurs, it is usually treated by injection of penicillin or some other antibiotic.

A variety of products are currently available for prophylactic use in controlling mastitis. Generally, these products are liquid preparations of some topical antiseptic such as chlorhexidene, iodine, sodium hypochlorite or a quaternary ammonium compound. These products are normally applied as dips to the animal's teats immediately after milking and are meant to disinfect the teat and protect it from infection. Although some of these disinfectant dips have a degree of beneficial action, their efficacy is limited by several factors. Firstly, these disinfectants do not form protective films on the teat with barrier properties, thus providing no protection from irritation by wind, sun and abrasion. Secondly, disinfectant dips have a short residual time on the teat, and their efficacy is quickly lost due to volatilization, oxidation and/or simply sloughing off. Furthermore, disinfectant dips fail to retard the entrance of bacteria into the teat canal, which is the major route of entry of infectious bacteria into the teat.

Heretofore, several attempts have been made to provide teat dips containing film-forming materials designed to form protective films on the skin of the teats. U.S. Pat. No. 3,066,071 discloses a method of coating the teats of cattle with a pliable, peelable film of, for example, a mixture of polyvinyl acetate and polyvinyl chloride. Typically the film is applied from a volatile solvent such as ethyl acetate or as a hot melt of the coating composition. Disadvantages of this method include subjecting the skin of the teat to the drying, irritating effects of organic solvents or hot materials.

U.S. Pat. No. 3,222,252 describes a bovine teat dip consisting of vegetable oils of the drying or semi-drying types and certain fatty acid esters. In practice, oil based dips have proved to be ineffective in preventing mastitis and they are difficult to remove from the teats with a water wash. In fact, their use has tended to increase the incidence of mastitis. (See J. Dairy Science, Dec. 1975 and Proc. Nat. Mastitis Council Feb. 10–12, 1975).

An effective nonirritating and long lasting teat dip which is water removable and which provides a physical barrier to bacterial penetration of the teat canal has long been desired. Heretofore such a dip has been considered to be impractical because of the many technical problems involved. (See "A Report of the Coliform Mastitis Research Committee," National Mastitis Council, Inc., Washington, D.C. 20006 January, 1975).

The present invention overcomes the disadvantages associated with prior art teat dips, and provides dips which are practical to use and afford continuous protection against mastitis.

The present invention provides both a composition and method for the prophylactic treatment of mastitis. The composition is nonirritating to the skin of the teat and comprises a film-forming polymer latex and a water soluble polymer thickening agent in an aqueous medium. The thixotropic properties and viscosity of the composition are important in order to achieve proper coating of the teat, and the composition should have a thixotropic value (as defined hereinbelow) of 15 to 1200 dynes/cm$^2$ and a practical upper viscosity limit of 10 poise at a shear rate of 250 sec$^{-1}$.

Compositions of the invention can be coated smoothly onto the teats by dipping with little or no dripping. They generally dry in approximately 20 minutes or less and form a continuous protective film over the skin of the teat and across the orifice to the teat canal. The film is durable, lasting from milking to milking without being easily rubbed off by the animal during its normal daily routine, yet is readily removed with water by the farmer during his normal pre-milking procedures. When wet, the film is visible on the teat so that the farmer can observe that all of the film is removed prior to milking. Teat dips of the invention are highly efficacious in inhibiting the transport of pathogenic organisms into the teat canal and also in protecting the skin of the teat from irritation caused by exposure to harmful environmental factors.

Water soluble polymers useful as thickening agents in the compositions of the invention are basically of two general classes, natural or synthetic. Naturally occurring water soluble polymers have been known for many years. Many are obtained from seeds, seaweeds or as exudates from trees, and have been extensively used as thickening agents in cosmetics, pharmaceuticals, etc. Water soluble polymers obtained from natural sources normally require little processing other than collection, grading, extraction, or purification, although minor chemical modifications are sometimes carried out to improve their properties. Examples of natural water soluble polymers include guar gum, gum arabic, gum tragacanth, larch gum, gum karaya, locust bean gum, agar, alginates, carageenan, pectins, and gelatin.

Synthetic water soluble polymers include the modified (or semisynthetic) polymers which are derivatives of cellulose and those which are completely synthetic. Cellulose is not water soluble without modification. However, a broad spectrum of products with varying degrees of water solubility may be synthesized by varying the molecular weight of the cellulose and the type and extent of substitution. Typical cellulose derivatives include methyl, hydroxyethyl, sodium carboxymethyl and combinations thereof.

Completely synthetic water soluble polymers can be prepared by direct polymerization of suitable monomers. Poly(vinylpyrrolidone), poly(acrylic acid), poly(acrylamide), poly(vinyl methyl ether), poly(ethylene oxide), and poly(ethyleneimine) are all water soluble polymers synthesized by direct polymerization.

The thickening agent of the compositions of the invention may include a mixture of water-soluble polymers. The water soluble polymer is usually present in an amount ranging from 0.1 to 5.0 percent by weight of the composition, with the optimum concentration usually being from 0.5 to 1 percent by weight. The optimum concentration for any particular water soluble polymer is achieved when the composition exhibits the proper rheological and water removability properties.

The compositions must have sufficiently low viscosity to allow easy application to the teats by dipping, yet they must not be so thin as to drip off the end of the teat. It is desirable for the compositions to flow slightly down the teat following application to form a thicker plug at the bottom of the teat across the orifice of the teat canal. This plug provides an effective barrier against bacteria entering the teat canal. Generally, the optimum viscosity and flow properties of the compositions can be achieved by varying the concentration of the water soluble polymer.

The concentration of water soluble polymer in the compositions also determines the extent to which the dried films are removed from the teat with water. Since the protective film must be removed from the teat prior to milking, it is desirable that the film be sufficiently water sensitive so as to be removed by the farmer during his normal premilking routine, e.g., by using plain water and a wash cloth. However, the film must not be so water-sensitive that it is removed by the animal, for example, when the animal lies in wet grass or walks through a stream. Generally, the degree of water sensitivity of the film increases as the concentration of water soluble polymer is increased.

Water-soluble polymer thickening agents which are preferred in the compositions of the invention are polysaccharide thickening agents, i.e., carbohydrates containing more than three molecules of simple sugars. Polysaccharide thickeners include gums, caragheenans, alginates, dextrans, starches, cellulose derivatives, etc. and combinations thereof. The polysaccharide thickening agent which is particularly preferred is xanthan gum, defined as exocellular biopolysaccharides produced in a pure culture fermentation process by the microorganism *Xanthomonas campestris*. Xanthan gum is commercially available from the Kelco Company under the trademarks "Keltrol" (food grade) and "Kelzan" (industrial grade). Xanthan gum in combination with sodium alginate is an especially preferred thickening agent for compositions of the invention.

The second major ingredient of the compositions of the invention is a film forming polymer latex. The term "polymer latex" as used herein refers to a suspension of a water insoluble polymer in water. In this context "polymer" refers broadly to homopolymers and polymers formed from two or more different monomers. Commercially available latexes generally include stabilizers, preservatives, suspending agents, etc. in minor amounts in addition to the polymer. Those ingredients necessary to the stability of the latex are included within the term "polymer latex."

The polymer latex should have a minimum film-forming temperature below 38° C., i.e., bovine body temperature. Minimum film-forming temperature is defined as the lowest temperature at which the polymer latex will form a film when thinly applied to a surface. It is preferable to have polymers with glass transition temperatures (Tg's) between 0° and 35° C. Polymers with lower glass transition temperatures are usually too tacky and those with higher glass transition temperatures are too brittle. A method for determining glass transition temperatures utilizes differential thermal analysis as found in Bacon Ke, editor, *Newer Methods of Polymer Characterization*, Interscience, New York, 1964, P. 396 and references cited therein. Illustrative polymer latexes having suitable film-forming characteristics include latexes of styrene butadiene, acrylic polymers and acrylic copolymers. Preferred polymer latexes include those of ethyl acrylate/methyl methacrylate copolymers, methyl methacrylate/butyl acrylate copolymers and styrene/butadiene copolymers. An especially preferred material is an ethyl acrylate/methyl methacrylate copolymer such as that available from Rohm and Haas Co., (Philadelphia, Pa.) as Primal ® B-52.

Some water insoluble polymers may require the inclusion of plasticizers so that the resulting film is sufficiently flexible to be useful and the polymer has a minimum film-forming temperature of less than 38° C. Plasticizing agents which are non-toxic to the skin can be added during the formation of the latex or by other suitable means, i.e., at any time during the processing of the compositions of this invention. When a plasticizer is included in the compositions of this invention, it may be either an external plasticizer or an internal plasticizer.

The polymer latex (including polymer, water and minor ingredients) preferably provides from 1 to 90 percent by weight of the composition. The optimum concentration of polymer latex has been found to be between 10 and 35 percent by weight. The remainder of the composition is made up of the water soluble polymer, water and any additives such as preservatives. Commercially available latexes generally contain from 38 to 56 percent solids. Thus, there is some dilution of the commercial latex during the preparation of the compositions.

The compositions of the invention may be prepared by adding the water soluble thickening agent to water (preferably containing preservatives) which has been heated to a temperature of 80° to 100° C. and stirring until the thickening agent is dissolved. The solution is then cooled to about 50° C. and the polymer latex is added slowly with stirring. The resulting product is a smooth, homogenous liquid.

Preservatives such as methyl paraben, propyl paraben, imidazolidinyl urea, or other nonirritation preservatives which are compatible with the other ingredients in the compositions are typically added to the compositions in small amounts, e.g., 0.1 to 1.0 percent by weight of the composition, to retard bacterial growth and prolong usefulness of the compositions. When xanthan gum is used as the thickening agent, quaternary ammonium compounds should be avoided as preservatives as they are incompatible with the xanthan gum.

The compositions of the invention may optionally include emollients, antimicrobials, dyes, medicaments, sunscreens, etc. which are compatible with the other ingredients of the composition. For prophylactic treatment, antimicrobials, medicaments, and other additives which tend to irritate the sensitive skin of the teat or which may result in possible milk contamination should be avoided. However, the incorporation of antiseptics such as alcohol, chlorhexidene, iodine, 8-hydroxy quinoline sulfate, sodium hypochlorite, etc. as well as other antimicrobial agents such as gentian violet, neomycin sulfate or tetracycline hydrochloride may be of benefit in certain infectious states. Anti-inflammatory agents such as hydrocortisone and sunscreens such as para-amino benzoic acid may also be beneficial in some cases.

Compositions of the invention are applied to the teats, preferably after each milking, by dipping the teat into the liquid composition. The compositions dry to a uniform protective film in approximately 20 minutes or less. The compositions must have certain rheological properties in order to insure proper application to the teat by dipping. It has been found that the proper rheological properties can be achieved by controlling the thixotropy and viscosity of the compositions.

Thixotropy and viscosity can be measured using standard methods employed in the latex paint industry. The "cone and plate" method described in Journal of Paint Technology, Vol. 41, No. 533, June, 1969, p. 395, is the particular method selected to measure the thixotropy and viscosity of the compositions of the invention. A "Mechanical Spectrometer" (made by Rheometrics, Inc., Union, N.J. 07083) having a 50 mm diameter flat plate is the instrument used in the test. The cone angle is 0.04 radians. An excess of test material is placed on the plate, the cone is lowered to 50 mm from the plate and excess test material is squeezed out. The cone is then rotated at continuously increasing velocities up to 100 radians per second in a time period of 50 seconds.

An x-y recorder is attached to the instrument and automatically plots viscous retarding torque vs. rotation. The recorder is calibrated in cgs units. The shear stress of the test material, measured in dynes/cm$^2$, is determined from the viscous retarding torque exerted on the rotor by the sample using the equation $$S = 3M/2\pi R^3$$

where $S$ is shear stress
$M$ is retarding torque
$R$ is the radius of the cone
The shear rate, measured in seconds$^{-1}$, is related to the angular velocity of the cone and cone angle by $$r = V/\beta$$

where $r$ is shear rate
$V$ is angular velocity
$\beta$ is cone angle.

A curve is obtained for each test material plotting shear stress against rate of shear using the values from the x-y recorder converted using the above equations. A typical sample curve is shown in the accompanying drawing.

The "yield point" for each test material was taken from an extrapolation of the shear rate to zero. For purposes of this invention yield point is synonomous with thixotropic value.

Using the test method described above, it was found that the compositions of invention must have a thixotropic value between 15 and 1200 dynes/cm$^2$. Those having a thixotropic value below the range tend to drip off the teats. Those above the range tend to be too viscous. Preferred compositions have a thixotropic value between 50 and 500 dynes/cm$^2$, and most preferred compositions have a thixotropic value between 75 and 300 dynes/cm$^2$.

In addition to having a thixotropic value in the prescribed range, compositions of the invention must have a viscosity not exceeding 10 poise at a shear rate of 250 sec$^{-1}$. Compositions exceeding this value are generally too viscous to practically apply to the teats by dipping. The viscosity of the compositions is determined using the same test described above by dividing shear stress by shear rate.

The compositions are not irritating to the skin of the teats and can be used repeatedly without damage to the udder. When the compositions are applied to the teats and allowed to dry, the film provides an effective barrier against migration of bacteria into the teat canal.

Understanding of the invention will be facilitated by reference to the following non-limiting examples. Unless otherwise indicated all percentages are by weight.

The following commercial products were used in the preparation of compositions included in the following examples.

| Commercial Designation | Source | Composition | |
|---|---|---|---|
| Rhoplex AC 22 | Rohm & Haas Philadelphia, Pa. | 44.5% solids | 35% methyl methacrylate 65% ethyl acrylate |
| Rhoplex AC 34 | Rohm & Haas Philadelphia, Pa. | 46% solids | 32% methyl methacrylate 66% ethyl acrylate 2% methacrylic acid |
| Polyco 2619 | Borden Co. New York, N.Y. | 56% solids | preplasticized vinyl chloride copolymer |
| Polyco 2430 | Borden Co. New York, N.Y. | 48% solids | 70% styrene 30% butadiene |
| Polyco 2607 | Borden Co. New York, N.Y. | 55% solids | internally plasticized vinyl chloride copolymer |
| Primal B-47 | Rohm & Haas Philadelphia, Pa. | 50% acrylonitrile 38% ethyl acrylate 12% methyl methacrylate | |
| Poly Em 40 | Cosden Oil & Chem. Co. Big Spring, Texas | Polyethylene emulsion | |
| Primal B-52 | Rohm & Haas Philadelphia, Pa. | 40% solids | 62% ethylacrylate 28% methyl methacrylate |
| Keltrol | Kelco Co. Los Angeles, Calif. | Xanthan gum | |
| KelcoGel LV | Kelco Co. Los Angeles, Calif. | Sodium alginate | |
| Germal-115 | Sutton Lab., Inc. Roselle, N.J. | Imidazolidinyl urea | |
| Jaguar HP-11 | Steinhall Specialty Chem. New York, N.Y. | Guar gum | |
| PVP-I | Napp Chemicals | Povidone iodine | |

-continued

| Commercial Designation | Source | Composition |
|---|---|---|
| | Lodi, N.J. 07644 | |
| Cellosize QP 4400 | Union Carbide Corp. New York, N.Y. | Hydroxyethyl cellulose |
| Carbopol 940 | B.F. Goodrich Chemical Co. Cleveland, Ohio | Carboxypolymethylene |
| Polyox WSR Coagulant | Union Carbide New York, N.Y. | Ethylene oxide polymer |
| Polyox WSR 301 | Union Carbide New York, N.Y. | Ethylene oxide polymer |

EXAMPLE I

To a solution of 73.85 ml of deionized water were added 250 mg of Germal-115 (preservative), 200 mg of methyl paraben (preservative) and 100 mg of propyl paraben (preservative). While maintaining the solution at a temperature between 83° and 100° C., 400 mg of Keltrol ® and 200 mg of KelcoGel ® LV were added with stirring until dissolved. The solution was cooled to about 55° C. and 250 g of Primal B-52 were added slowly with constant stirring. Stirring was continued until a smooth, homogeneous product was obtained.

The product was tested according to the procedure described hereinabove and found to have a thixotropic value of 130 dynes/cm$^2$.

The safety and efficacy of the teat dip composition were evaluated by applying the dip to the teats of five milking cows over a period of eight months. The cows were housed in a warm barn (50° F.) and restrained in stanchions with sawdust bedding for the duration of the study. The cows were milked twice daily with commercial milking machines.

The udders were prepared for milking in the conventional manner by washing with a disinfectant solution. After each milking, the right front and rear teats of each cow were dipped in the test composition. The left teats were not dipped. The composition was allowed to dry on the teats for about five minutes. All four teats were then dipped in a milk suspension of *Streptococcus agalactiae* having a concentration of approximately 5 × 10$^6$ organisms/ml. Bacterial cultures were taken from each cow's milk weekly during the term of the study.

No irritation of the teats was observed over the eight month period of the study. In fact, teats dipped in the test composition appeared softer and in better condition than the undipped teats. A total of 397 bacterial cultures of milk were taken from the dipped sides of the udders and 341 from the undipped sides. Pathogenic organisms were isolated 13 times (3.3 percent) from the dipped side and 60 times (17.6 percent) from the undipped side. This is a good indication that the composition provides a physical barrier to bacteria entering the teat canal.

Following the method of Example 1 the following compositions were prepared:

Table I

| Example No. | Ingredient | Amount (percent by Wt) | Thixotropic Value |
|---|---|---|---|
| 2 | Keltrol | 0.4 | 95 |
| | KelcoGel LV | 0.2 | |
| | Rhoplex AC-22 | 20.0 | |
| | Water | to 100 | |
| 3 | Keltrol | 0.4 | 110 |
| | KelcoGel LV | 0.2 | |
| | Rhoplex AC-34 | 20.0 | |
| | Water | to 100 | |
| 4 | Keltrol | 0.4 | 95 |
| | KelcoGel LV | 0.2 | |
| | Polyco 2619 | 20.0 | |
| | Water | to 100 | |
| 5 | Keltrol | 0.4 | 110 |
| | KelcoGel LV | 0.2 | |
| | Polyco 2430 | 20.0 | |
| | Water | to 100 | |
| 6 | Keltrol | 0.4 | 90 |
| | KelcoGel LV | 0.2 | |
| | Polyco 2607 | 20.0 | |
| | Water | to 100 | |
| 7 | Keltrol | 0.4 | 625 |
| | KelcoGel LV | 0.2 | |
| | Primal B-47 | 20.0 | |
| | Water | to 100 | |
| 8 | Keltrol | 0.4 | 110 |
| | KelcoGel LV | 0.2 | |
| | Poly-Em 40 | 20.0 | |
| | Water | to 100 | |
| 9 | Jaguar HP-11 | 1.0 | 440 |
| | Primal B-52 | 20.0 | |
| | Water | to 100 | |
| 10 | Keltrol | 0.4 | 130 |
| | KelcoGel LV | 0.2 | |
| | Primal B-52 | 25.0 | |
| | Sodium Hypochlorite Solution (4-6%) | 1.5 | |
| | Water | to 100 | |
| 11 | Keltrol | 0.4 | 150 |
| | KelcoGel LV | 0.2 | |
| | Primal B-52 | 20.0 | |
| | PVP-I | 11.4 (to give 1% free iodine) | |
| | Water | to 100 | |
| 12 | Keltrol | 0.2 | 30 |
| | KelcoGel LV | 0.1 | |
| | Primal B-52 | 20.0 | |
| | Water | to 100 | |
| 13 | Keltrol | 2.0 | 750 |
| | KelcoGel LV | 1.0 | |
| | Primal B-52 | 20.0 | |
| | Water | to 100 | |
| 14 | Carbopol 940 | 1.0 | 1200 |
| | Primal B-52 | 20.0 | |
| | Water | to 100 | |
| 15 | Cellosize QP-4400 | 1.0 | 150 |
| | Primal B-52 | 20.0 | |
| | Water | to 100 | |

All compositions contain 0.55% preservatives (0.25% Germal-115, 0.2% methyl paraben and 0.1% propyl paraben).

Additional compositions were prepared using the following water soluble polymers and latexes. The numbers in the table indicate the percent by weight of the water soluble polymer. The polymer latex provided 25% by weight of the composition in all cases. All compositions contain 0.55% preservatives (0.25% Germal-115, 0.2% methyl paraben and 0.1% propyl paraben).

Table II

| | Primal B-52 | Rhoplex B-47 | Polyco 2430 |
|---|---|---|---|
| Gum Acacia | 1 | 1 | 1 |
| Dextran | 1 | 1 | 1 |
| Gum Tragacanth | 1 | 1 | 1 |
| Carragheenan | 1 | 1 | 1 |
| Agar | 2 | 2 | 2 |
| Gum Karaya | 2 | 1 | 1 |

Table II-continued

|  | Primal B-52 | Rhoplex B-47 | Polyco 2430 |
|---|---|---|---|
| Gum Ghatti | 1 | 1 | 1 |
| Starch | 2 | 2 | 2 |
| Guar Gum | 1 | 1 | 1 |
| Polyox WSR Coagulant | 1 | | |
| Polyox WSR 301 | 1 | | |
| Polyacrylamide | 1 | | |

What is claimed is:

1. A method for the prophylactic treatment of mastitis comprising dipping the teats of the animal into a composition comprising a polymer latex and a water soluble polymer thickening agent in an aqueous medium, said composition having a thixotropic value of 15 to 1200 dynes/cm$^2$ and an upper viscosity limit of 10 poise at a shear rate of 250 sec$^{-1}$; and said composition forming a continuous film on the teat which is durable enough to last from milking to milking and sufficiently water sensitive to be removed by wiping with a water-moistened cloth.

2. The method according to claim 1 wherein the water soluble polymer thickening agent is a polysaccharide.

3. The method according to claim 2 wherein the polysaccharide is xanthan gum.

4. The method according to claim 2 wherein the polysaccharide thickening agent is a combination of xanthan gum and sodium alginate.

5. The method according to claim 1 wherein the polymer latex is a latex of ethyl acrylate/methyl methacrylate copolymer.

6. The method according to claim 1 wherein the polymer latex is a latex of styrene/butadiene copolymer.

7. The method according to claim 1 wherein the composition further comprises an antimicrobial agent.

8. A nonirritating composition for the prophylactic treatment of mastitis comprising a polymer latex and a water soluble polymer thickening agent in an aqueous medium, said composition having a thixotropic value of 15 to 1200 dynes/cm$^2$ and an upper viscosity limit of 10 poise at a shear rate of 250 sec$^{-1}$; and said composition forming a continuous film on the teat which is durable enough to last from milking to milking and sufficiently water sensitive to be removed by wiping with a water-moistened cloth.

9. The composition according to claim 8 wherein the water soluble polymer thickening agent is a polysaccharide.

10. The composition according to claim 9 wherein the polysaccharide is xanthan gum.

11. The composition according to claim 9 wherein the polysaccharide thickening agent is a combination of xanthan gum and sodium alginate.

12. The composition according to claim 8 wherein the polymer latex is a latex of ethyl acrylate/methyl methacrylate copolymer.

13. The composition according to claim 8 wherein the polymer latex is a latex of styrene/butadiene copolymer.

14. The composition according to claim 8 further comprising an antimicrobial agent.

* * * * *